United States Patent [19]

Blumenthal et al.

[11] 4,186,072
[45] Jan. 29, 1980

[54] HOT GAS MEASURING DEVICE

[76] Inventors: Robert N. Blumenthal, 17470 Bard Ct., Brookfield, Wis. 53005; Andreas T. Melville, 204 N. 86th St., Milwaukee, Wis. 53226

[21] Appl. No.: 914,703

[22] Filed: Jun. 12, 1978

Related U.S. Application Data

[63] Continuation-in-part of Ser. No. 700,659, Jun. 28, 1976, Pat. No. 4,101,404.

[51] Int. Cl.$^2$ .................................................. G01N 27/58
[52] U.S. Cl. ................................................... 204/195 S
[58] Field of Search ............... 204/195 S, 1 S; 429/30, 429/31, 32, 33, 193; 123/119 E, 119 EC; 60/276

[56] References Cited

U.S. PATENT DOCUMENTS

| Re. 28,792 | 4/1976 | Ruka et al. | 204/1 T |
|---|---|---|---|
| 3,300,344 | 1/1967 | Bray et al. | 429/33 |
| 3,454,486 | 7/1969 | Davies | 204/195 S |
| 3,546,086 | 12/1970 | Sayles | 204/195 S |
| 3,597,345 | 8/1971 | Hickham et al. | 204/195 S |
| 3,922,204 | 11/1975 | Tseung et al. | 204/1 T |

FOREIGN PATENT DOCUMENTS

| 2401134 | 8/1974 | Fed. Rep. of Germany | 204/195 S |
|---|---|---|---|
| 1296995 | 11/1972 | United Kingdom | 204/195 S |
| 1352995 | 5/1974 | United Kingdom | 204/195 S |

OTHER PUBLICATIONS

D. B. Meadowcroft, Proc. Internat. Conf. on Strontium Containing Compounds, pp. 119-136, Jun., 1973.
D. B. Meadowcroft, Brit. J. Appl. Phys., Ser. 2, vol. 2, pp. 1225-1233, (1969).
R. N. Blumenthal et al., "Ceramics and Glass: Science and Technology," Part A, pp. 71-76, (1974).
R. W. Vest et al., "Ceramics and Glass: Science and Technology," Part B, pp. 370-375, (1974).
C. S. Tedmon, Jr. et al., J. Electrochem. Soc., vol. 116, No. 9, pp. 1170-1175 (1969).

Primary Examiner—G. L. Kaplan
Attorney, Agent, or Firm—Wheeler, Morsell, House & Fuller.

[57] ABSTRACT

A probe comprising a tube made of solid electrolyte material is slidably mounted within a ceramic support tube which is mounted to project into the interior of a furnace. The end of the electrolyte tube is closed and the support tube has open ports or windows therein which expose the exterior end surface of the electrolyte tube to the hot furnace gases and causes a voltage to develop between the interior and the exterior surfaces of the electrolyte tube which is indicative of a furnace gas characterstic. A first electrode is supported between the ends of the electrolyte tube and the support tube, and a second electrode is supported within the inner end of the electrolyte tube. To prolong the life of the electrode, it is preferably made either of multiple layers of noble metal wire screens mounted in face-to-face relationship, a chemically stable electronic ceramic conductor such as cation-doped lanthanum chromite, or a noble metal screen coated with an electronic conducting ceramic cement.

15 Claims, 10 Drawing Figures

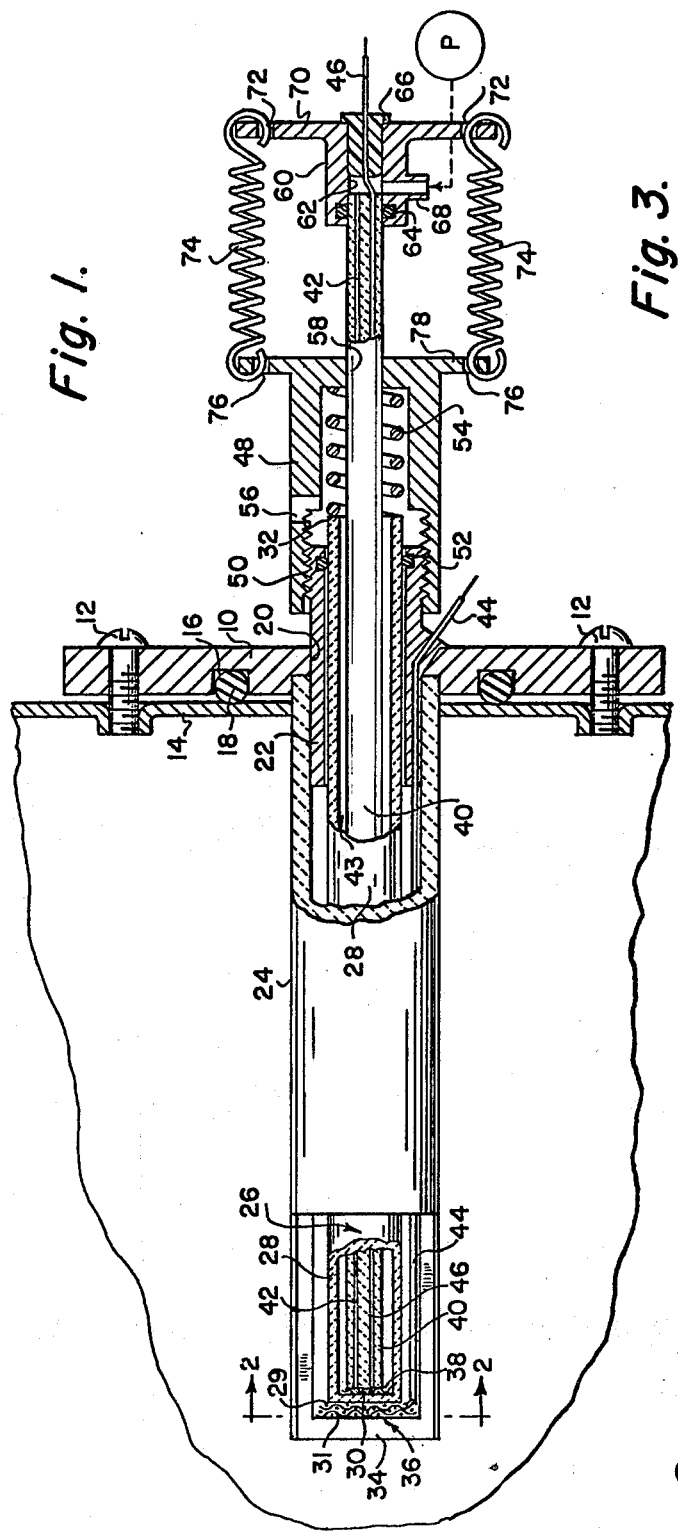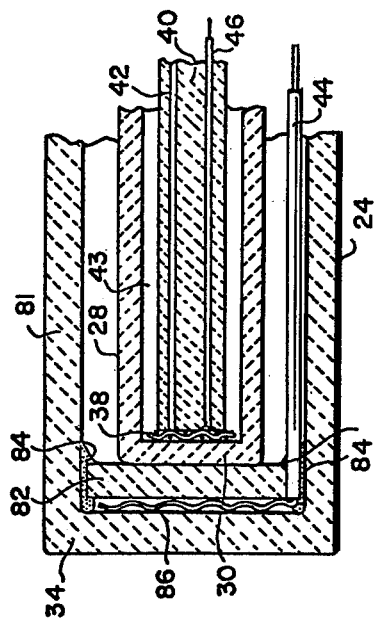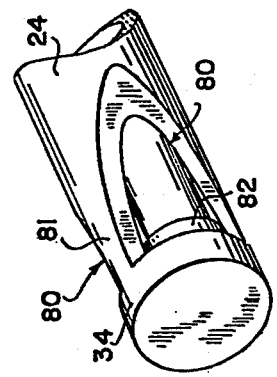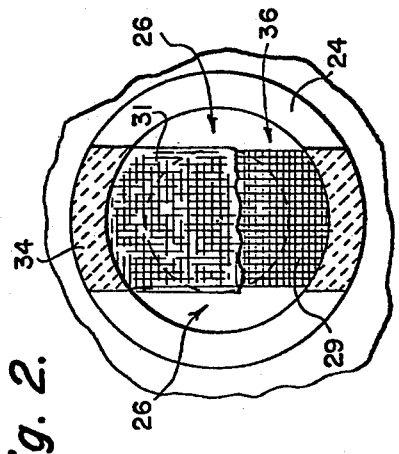

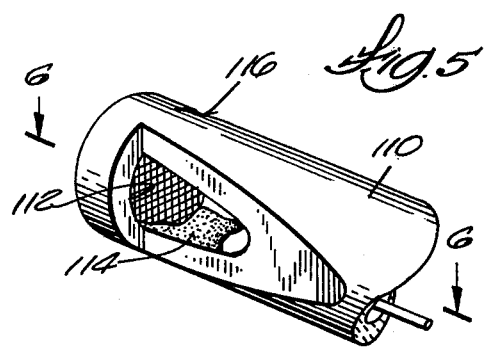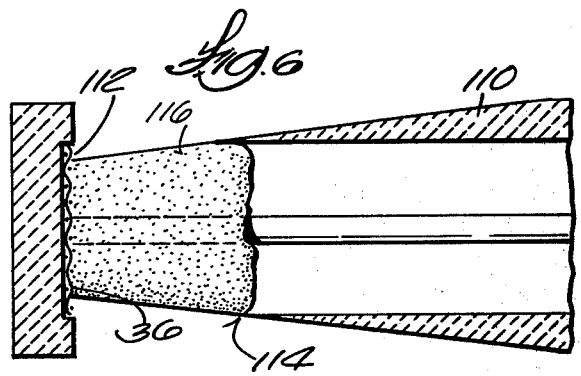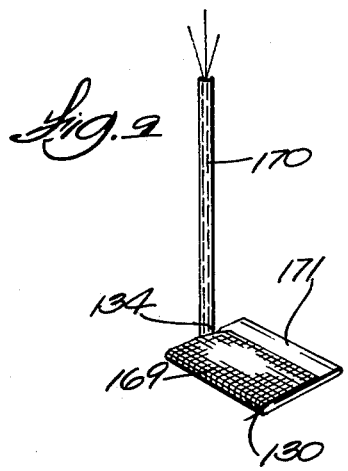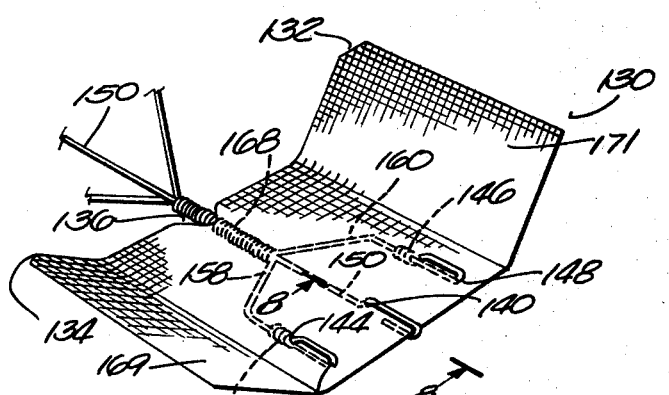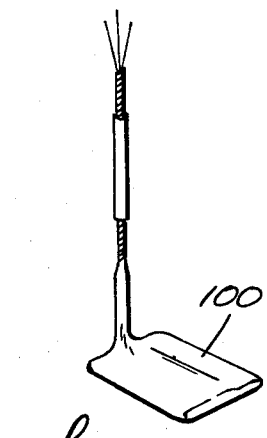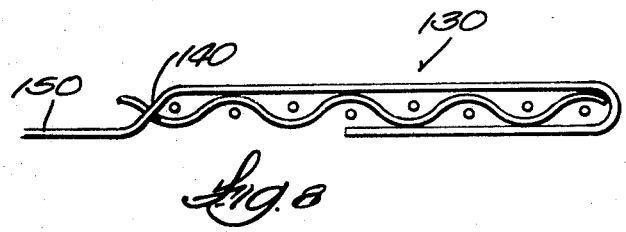

HOT GAS MEASURING DEVICE

CROSS REFERENCE TO RELATED APPLICATION

This application is a continuation-in-part of U.S. application Ser. No. 700,659, filed June 28, 1976, now U.S. Pat. No. 4,101,404.

BACKGROUND OF THE INVENTION

This invention relates to the measurement of gas characteristics through the use of a probe comprising a solid electrolyte which is in contact on one side or face with a reference gas such as the ambient atmosphere and is in contact on the opposing side or face with a hot gas whose characteristics are to be measured. In such a probe, a voltage is generated between the two sides or faces of the solid electrolyte, the magnitude of the voltage being dependent upon the temperature of the electrolyte and on the ratio of the oxygen partial pressure on opposing sides or faces of the electrolyte. This principle has been used in the past to measure the oxygen partial pressure of hot furnace gases with various different oxygen sensors, such as disclosed in U.S. Pat. Nos. 3,454,486; 3,546,086 and 3,597,345 and British Pat. No. 1,296,995.

Although the principle of operation of the above-noted type of oxygen sensors is quite simple, the utilization of such oxygen sensors in industrial applications has been limited in the past due to several practical problems. First, the solid electrolyte, which is a ceramic material, is hard and brittle and is thus very susceptible to thermal shock and/or mechanical damage. Another problem has been the detachment of the electrode from the surface of the electrolyte due to corrosion of the electrodes. The latter problem occurs even when the electrodes are made of a noble metal, such as platinum. For example, platinum reacts at high temperatures and low oxygen pressures with stabilized zirconia electrolyte material, which is commonly used in this type of oxygen sensor to form $ZrPt_3$. The reaction product is in the form of fragments or dust which drops away from the electrode, thus reducing the thickness thereof and eventually breaking the electrical contact between the electrode and the electrolyte or loosening the electrode sufficiently in its mounting to allow it to be blown away by the gas stream under measurement. The life of prior art electrodes is substantially reduced when used in a highly corrosive atmosphere typically present in some heat treating furnaces. For the above reasons, the useful working life of the above-noted type of oxygen sensor has been limited in the past and has limited their potential range of application.

The use of an electronic ceramic coating is disclosed in U.S. Pat. No. Re. 28,792. This patent discloses (Col. 6, lines 19–66) an electrode for a fuel cell using an electronic conducting porous metal oxide coating. However, the type of electrode disclosed in U.S. Pat. No. Re. 28,792 requires that the electrodes 12 and 14 which are applied directly to the electrolyte be porous so that gas can readily diffuse through the electrodes to the electrolyte interface 10 (U.S. Pat. No. Re. 28,792, Col. 3, lines 48–68; Col. 4, lines 1–8). This arrangement requires a somewhat critical and low contact resistance (Col. 6, lines 19–20) for effective operation. Inasmuch as the present invention is an open circuit sensor, the contact resistance is not as critical for good operation. It is difficult to obtain uniform porosity with coatings. If the coating is too thick and does not have sufficient porosity, electrode polarization can occur which will affect output of the cell. If the coating is too thin, the resistance may be too high for proper operation. The disadvantages and critical requirements of electronic conducting coatings applied directly to the electrolyte are discussed in the article "Cathode Materials and Performance in High-Temperature Zirconia Electrolyte Fuel Cells" in the Journal of the Electrochemical Society, Vol. 116, pages 1170–1175 (1969). Use of a disc or other element formed from electronic conducting ceramic as an electrode in accordance with the invention eliminates the need for porosity in a coating applied to an electrolyte as taught by the prior art. The mechanical clearance between the electronic conducting ceramic electrode and the electrolyte enables accessibility of the furnace gases.

SUMMARY OF THE INVENTION

The principal object of this invention is to provide a novel gas measuring device which has a longer working life than those heretofore known. In accordance with this invention, the problem of electrode corrosion is solved in one embodiment of the invention by forming the outer electrode which is exposed to the hot furnace gases from a noble metal mesh screen, with the screen folded over upon itself to form multiple layers. This arrangement increases the over-all thickness of the electrode so that as the wires disintegrate and flake off, there will be ample reserve electrode wire remaining to function as a conductor. Even though there are several layers, the mesh form of the wires provides for flow of gas through the electrode. The undulating configuration of the wires in the mesh provides many points of contact between one mesh and the next, and with the electrolyte. The electrode is spring loaded to continually press one mesh screen against the other, and with the electrolyte, thus to take up any void space as the electrode wire disintegrates and fragments thereof drop off or are blown off. A modified embodiment of the mesh screen electrode includes a mesh screen with wing portions folded in overlapping relation upon a central web portion. Thus two overlapping layers of screen protect the lead wire connections to the mesh.

In another embodiment of the invention, the electrode comprises a chemically stable electronic ceramic conductor in the form of a disc which is relatively inert with respect to known hot furnace gases and known solid electrolytes and to the electric lead wires coupled thereto. The use of a disc or other suitably shaped or formed disc rather than a porous electronic conducting coating applied directly to the electrolyte eliminates the various problems with electronic conducting coatings as noted above. A further modified embodiment of the invention comprises a mesh screen or metallic conductor coated with a non-porous or impervious electronic conducting ceramic coating. The protective coating prevents the deterioration of the metallic parts of the electrode and lead wire where hot corrosive gases are present. The coating should be sufficiently thick or be applied in a manner to eliminate open porosity to prevent corrosion to the metallic parts and lead wire.

The above-mentioned electrode embodiments substantially extend the working life of the electrode and enable the oxygen sensor to be applied to industrial applications which were heretofore impractical because of the relatively short working life of prior art electrodes.

Other objects, features and advantages of the invention will appear from the disclosure hereof.

DESCRIPTION OF THE DRAWINGS

FIG. 1 is a side view of one embodiment of the probe mounted to extend within a furnace, various portions of the probe being partially cut away and shown in longitudinal section to reveal inner details.

FIG. 2 is a cross sectional view taken on the line 2—2 of FIG. 1.

FIG. 3 is a fragmentary enlarged longitudinal sectional view of a modified embodiment of the invention in which the electrode comprises an electronic ceramic disc.

FIG. 4 is a fragmentary perspective view of the end of the probes of the FIG. 3 embodiment.

FIG. 5 is a fragmentary perspective view of a modified embodiment of the support tube.

FIG. 6 is an enlarged sectional view along line 6—6 of FIG. 5.

FIG. 7 is a perspective view of a modified mesh electrode in an unfolded condition.

FIG. 8 is a sectional view along line 8—8 of FIG. 7.

FIG. 9 is a perspective view of the folded mesh electrode shown in FIG. 7.

FIG. 10 is a view similar to FIG. 9 with the electrode coated with an electronic conducting ceramic cement.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIG. 1, the mounting structure for this embodiment includes a circular metal flange 10 which has holes formed in the periphery thereof to receive bolts 12 for fastening flange 10 to a port 14 on the side wall of a furnace. A circular groove 16 is formed in the inner surface of flange 10 for receiving an O-ring 18 which acts as a gas seal. Welded in the center of flange 10 is a metal sleeve 22 which supports a ceramic support tube 24 that extends into the interior of the furnace. Support tube 24 has cut away portions which form open ports or windows 26 on opposing sides of tube 24 near its end. A smaller tube 28 which is made of a solid electrolyte material and has a closed end 30 adjacent ports 26 of tube 24 inside the furnace and an open end 32 outside the furnace is slidably mounted within metal sleeve 22 and extends through support tube 24 and terminates near the bottom end 34 thereof.

Electrolyte tube 28 is preferably made of calcia stabilized zirconia although other electrolytes could be used such as $Y_2O_3$ stabilized zirconia, calcia-doped thoria, etc. However, the calcia-stabilized zirconia is preferable because it is believed to possess better thermal shock characteristics than the other common solid electrolyte materials. The ceramic material used for support tube 24 is preferably alumina, which has good thermal shock characteristics and also has a coefficient of thermal expansion which closely matches that of the calcia-stabilized zirconia.

A first electrode 36 is mounted between the outer face of the inner end 30 of electrolyte tube 28 and the inner face of the end wall 34 of support tube 24. A second electrode 38 is mounted on the opposite side of the end wall 30 of electrode tube 28 between the inner face of said end wall 30 and the end of a ceramic rod 40 mounted with electrolyte tube 28. Ceramic rod 40 is preferably made of alumina and has one or more longitudinal bores 42 through which a reference gas such as the ambient atmosphere is admitted to the interior face of electrolyte end wall 30 while the exterior face thereof is in contact with the hot furnace gases admitted through ports or windows 26. The reference gas is fed to bore 42 through side port 68 (FIG. 1) and is exhausted through the space 43 about the tube 28 and through its open end 32. As noted above, when the interior surface of electrolyte tube 28 is exposed to a reference gas and the exterior thereof is exposed to the host gases which are to be measured, a voltage is generated between the exterior and interior surfaces of the electrolyte tube end wall 30. The magnitude of the voltage is dependent upon the temperature of the electrolyte material and the oxygen partial pressure ratio between the opposing sides of the electrolyte. Electrodes 36 and 38 serve the function of picking up this voltage difference and conducting it via suitable ceramic insulated conductors 44 and 46 to a suitable conventional measuring instrument (not shown) located at the exterior of the device.

The structure of the first electrode 36 is particular important in this invention because it is exposed to the hot furnace gases and also is pressed against the end wall 30 of the electrolyte tube 28. Electrode 36 is subject to be corroded either by reaction with some component of the furnace gases or by reaction with the end 30 of the electrolyte tube 28. In accordance with one aspect of this invention, the problem of loss of electrical contact due to such corrosion is obviated by providing an improved electrode structure which either resists such corrosion, or which renews itself as it corrodes, thus to negate the deleterious effects of such corrosion. Such an electrode is subject to the load of an improved bias spring assembly which urges the end wall 30 of electrolyte tube 28 against the electrode 36, thus to maintain good contact therebetween in spite of such corrosion.

One embodiment of electrode is shown in FIGS. 1 and 2. It consists of two or more platinum wire screens 29, 31 which are welded or otherwise held together in face-to-face contact or assembly 36 with each other. The planes of the assembled screens 29, 31 are transverse to the axis of electrolyte tube 28. The undulations of the wires in screens 29, 31 provide good point contact of one screen with the other and with the electrolyte. By having more than one screen layer, there will be ample reserve of electrode wire which will continue to function even as the wire corrodes or disintegrates and fragments thereof flake or dust off. The spring loading on electrolyte tube 28 causes electrolyte tube 28 to advance toward electrode 36 as the contact portions of the platinum in the electrode 36 react with the zirconia in the electrolyte tube 28 to cause disintegration of the electrode and gradual reduction of electrode thickness and thus maintains good electrical contact with the platinum screen electrode assembly 36 even though corrosion does occur. The reaction product which is formed between the platinum wire electrode and the end of the electrolyte tube 28 is typically in the form of a dust which falls downwardly from the screen and exposes fresh platinum for electrical contact purposes. Mesh screens 29, 31 can be fabricated of noble metal or noble metal alloy wires other than platinum, for example, the platinum-rhodium alloy wires, gold wires and god-palladium alloy wires referred to in British Pat. No. 1,296,995.

Electrode 38 is also desirably a noble metal mesh screen, but it need only comprise a single layer screen rather than a multiple layer screen because the relatively high oxygen pressure in the atmosphere which contacts the electrode 38 inhibits the corrosive reaction thereof against the electrolyte tube 28 and screen 38 is not exposed to the hot gases in the furnace. Accordingly, screen 38 is not as subject to corrosion and disintegration as is electrode 36.

The compressive load is maintained between electrolyte tube 28 and electrode 36 by means of an improved spring mounting assembly which includes a hollow cylindrical cap 48 which is threaded to the outer end of sleeve 22 by screw threads 50. The hot gases which are admitted to the interior of support tube 24 are prevented from entering cap 48 by means of an O-ring seal 52 between electrolyte tube 28 and sleeve 22. A compression spring 54 is mounted interiorly within cap 48 and bears against the outer end 32 of electrolyte tube 28 and thus urges electrolyte tube 28 against electrode 36. The amount of pressure of spring 54 can conveniently be adjusted by simply turning cap 48. A viewing port 56 is formed in central portion of cap 48. By observing the position of spring 54 through port 56 as cap 48 is being turned, the operator can perceive an approximate indication of the amount of change of spring pressure for a given amount of turning, and the compression of the spring. If desired, a more accurate scale could be marked on the cap 48 and the adjacent portion of sleeve 22.

Cap 48 has a central opening 58 in its outer end through which ceramic rod 40 slidably extends. A cap 60 is mounted by O-ring 64 on the outer end of rod 40. Cap 60 has a central bore 62 which is sealed against rod 40 on its inner end by an O-ring 64 and is plugged on its outer end by a flexible insulating plug 66 through which electrical conductor 46 extends. A gas inlet port 68 extends from the side wall of sleeve 60 and communicates into bore 62 for introducing a reference gas such as the ambient atmosphere into the interior of electrolyte tube 28 via one or more of the longitudinal bores 42 in rod 40. The reference gas which is thus introduced into the interior of electrolyte tube 28 escapes through the open end 32 thereof and the opening 56 in cap 48.

Sleeve 60 has a circular flange 70 on its outer end which has two openings 72 formed on opposing sides thereof for receiving the ends of springs 74 which are secured at their other ends to openings 76 in a flange 78 on the outer end of end cap 48. Springs 74 urge rod 40 inwardly against electrode 38, thus to maintain good contact between electrode 38 and the closed end 30 of electrolyte tube 28. It should be noted that when the end cap 48 is rotated to change the tension of spring 54, the tension is also changed on the springs 74 in the same direction, i.e. when cap 48 is turned in a direction to increase the pressure on first electrode 36, the pressure on second electrode 38 is also increased, and vice versa.

FIGS. 3 and 4 show a modification in which the electrode between the electrolyte 28 and the end wall 34 of tube 24 comprises an electronic ceramic conductor. In this modification, open windows or ports 80 are cut transversely to the longitudinal axis of tube 24 in opposite sides of tube 24 to expose portions of the side edges of a disc-shaped electronic ceramic electrode 82. End wall 34 of tube 24 remains connected to the main body of tube 24 by bridges 81. Electrode disc 82 is cemented by refractory cement 84 into the closed end 34 of support tube 24 over the top of a wavy platinum wire 86 which is connected to the end of conductor 44, which serves to make contact with the outer face of electrode disc 82. The refractory cement 84 completely seals around the entire periphery of the electrode disc 82 so as to isolate and seal the platinum wire 86 from contact with the hot furnace gases. However, the hot furnace gases do contact the inner surface of electrode disc 82 and the outer surface of the end wall 30 of electrolyte tube 28, thus to generate a voltage difference between electrodes 38 and 82.

The electronic ceramic electrode is compounded of a suitable electronic ceramic conductor means which meets the following requirements:

(a) high electronic conductivity;
(b) chemical and thermodynamic stability;
(c) it should be relatively inert to the electrolyte, the hot furnace gas and the electric lead wire 86 (typically platinum) which is coupled thereto.

Electronic ceramic conductor means meeting these requirements are discussed in detail in the scientific literature, for example, in the book entitled "Electrical Conductivity in Ceramics and Glass " published by Marcel Dekker, Inc. in 1974, Parts A and B, Edited by N. M. Tallan, see particularly Chapter 6, "Highly-Conducting Ceramics and the Conductor-Insulator Transition", and the article of D. B. Meadowcroft in the British Journal of Applied Physics of 1969, Ser. 2, Vol. 2, page 1225, et seq. entitled "Some properties of strontium-doped lanthanum chromite". There are a number of electronic ceramic conductors suitable for use as electrode 82; for example, many of the rare earth perovskite oxides $RTO_3$, where R is rare earth or yttrium and T is a transition metal, are suitable. Meadowcroft has reviewed some of the properties and applications of "doped" and pure rare earth perovskites. This review is contained in Proceedings of the International Conference on Strontium containing compounds Halifax, Nova Scotia, June 1973, edited by T. J. Gray, "Some Properties and Applications of Strontium-Doped Rare Earth Perovskites". The rare earth perovskites can be described as the series $RTO_3$ where R is a rare earth—Ce,Pr,La,Gd, etc. (and also Y)—and T is a transition metal—CO,Mn,Fe,Cr,Ni,Ti,V. Although the rare earth and transition metal must be present primarily tri-valent ions, the electronic conductivity of these compounds can be enhanced by doping with suitable aliovalent cations. Both higher or lower valent cations may be used substituting for either the rare earth or the transition metal ions.

Of the various electronic ceramic conductors which are suited for use as electrode 82, we prefer cation-doped lanthanum chromite compounded by the formula $La_{1-x}M_xCrO_3$ where M can be any cation having a valence of +2 such as calcium, strontium, magnesium, or the like. The operative range of values for x is between 0 and 0.25. The above-noted compound solves the problem of electrode corrosion because it is substantially inert to known furnace gases, known solid electrolytes and the noble metal contact wire 86, it has good electrical conductivity and is chemically and thermodynamically stable.

Within the operative range of values for x given above, the preferred range is between 0.15 and 0.25.

The electrode 82 disclosed in FIGS. 3 and 4 is in the form of a disc molded or formed from the electronic ceramic conductor. Slight mechanical clearance between the abutting surfaces of electrode 82 and end 30 of the electrolyte tube enables the gas to be measured to move between these surfaces.

Referring again to FIG. 1, the reference gas is pumped by a conventional pump P into port 68 and flows down the bores 42 in rod 40 to the inner end 30 of electrolyte tube 28 and then flows back in the space between the inner surface of tube 28 and the outer surface of rod 40 and is discharged into the atmosphere through opening 56 in cap 48. This is an important feature of the invention because in some instances small cracks will form in electrolyte tube 28 and will admit the furnace gases to the interior of tube 28. Such leaked gases mix with and contaminate the reference gas and produce inaccurate output signals. However, with the above-described routing of the reference gas stream, the leaked gases are flushed by the reference gas stream away from the end 30 of electrolyte tube 28 where the potential difference is measured. Therefore, the reference gas adjacent to end 30 of electrolyte tube 28 is uncontaminated and produces accurate output signals even when there is leakage of gas through other portions of tube 28.

In another embodiment of the invention, illustrated in FIG. 10, the platinum screen electrode and platinum lead wire are coated with a protective coating 100 of an electronic conducting ceramic. The protective coating prevents the deterioration of the electrode by isolating the platinum electrode and lead wire from the hot corrosive gases. In this case the protective coating of an electronic conducting ceramic acts as the electrode and also makes electrical contact with the platinum screen and lead wire. With this arrangement no correction has to be made for thermal emfs since both electrodes are at the same temperature and the lead wires are made of the same material.

The protective coating may be prepared by mixing the powder of the electronic conducting ceramic with a commercially available alumina cement such as AREMCO ULTRA BOND$^{TM}$552, coating the platinum screen and platinum wire, air drying and then firing at an elevated temperature in air (e.g. 1100° C. for approximately 2 hrs.)

We have found that the preferred mixture is 50–75% by volume of the electronic ceramic material (e.g. $La_{0.84}Sr_{0.16}CrO_3$) and 50–25% by volume of the commercially available alumina cement.

FIGS. 5 and 6 show a modified embodiment of the support tube 110 which includes a recess 112 which is open to the windows 114, 116 and which assists in positively positioning and retaining a mesh electrode 36 in the support tube and also facilitates assembly of an electrode 36. The screen is cemented in the recess 112 by a ceramic cement. The ceramic cement is desirably the same material as the support tube 24 so that no stresses occur due to different coefficients of expansion.

FIGS. 7, 8 and 9 disclose a modified embodiment of the mesh screen electrode 130. The electrode is formed from a sheet of platinum wire mesh which desirably has notches 132, 134 and 136. Holes are formed in the screen at 140, 142, 144, 146 and 148. A main lead wire 150 is extended through hole 140, looped around the end of the screen and folded over upon the screen.

Good electrical connection of the lead 150 with the mesh screen is afforded by the use of lead wires 158 and 160. The wire 158 is looped through the holes 142, 144 in the web portion of the screen 130 and the end of the wire is wrapped around itself at 164. The wire 158 is wrapped around the lead wire 150 at 168. The wire 160 is similarly extended through openings 146 and 148 and wrapped around the wire 150. The wires 158, 160 are wrapped a distance up the lead wire as illustrated in FIG. 7 to make a good electrical contact therewith. The wings 169, 171 of the mesh are then folded over as illustrated in FIG. 9, with wing 169 overlapping the wing 171. A tubular ceramic sheath 170 can then be arranged around the lead wire for protection thereof. The embodiment illustrated in FIG. 10 can be the electrode shown in FIG. 9 with a coating of electronic conducting ceramic as previously described. Alternatively, the electrode can comprise a metallic conductor coated with the electronic conducting ceramic. More specifically, the metallic conductor could be a single screen or coil, etc.

The notches 132, 134, 136 enable the lead wire 150 to be recessed within the outline of the mesh screen. The notch helps support the lead wire and the screen zone around the notch provides a good base for the ceramic illustrated in FIG. 10 which rigidifies the lead wire-screen assembly.

The use of a solid electronic ceramic disc or a mesh electrode coated with electronic ceramic cement is preferred where there is a highly corrosive atmosphere such as that found in heat treating furnaces where there are chlorine or sulfur gases produced by cutting oils, cleaning fluid such as trichloroethylene or alkaline cleaners, etc. that accompany the parts that are processed in the furnace.

What is claimed is:

1. A gas measuring device for measuring a characteristic of high temperature gases comprising an electrolyte tube having an inside surface and an outside surface, said tube comprising a solid electrolyte material, mounting means for so mounting said tube that one of said surfaces is exposed to a hot corrosive gas whose characteristic is to be measured and the other said surface is exposed to a known reference gas, a first electrode, means for holding said first electrode in contact with said one surface, a second electrode, means for holding said second electrode in contact with said other surface, electrical conductors coupled to said electrodes, said mounting means including a bracket for fastening the device to the furnace wall and including an axially projecting sleeve concentric with the tube and attached to the bracket to provide support for said tube remote from said one end of said electrolyte tube for guiding said electrolyte tube for axial sliding movement within said sleeve and to afford axial shifting of said tube to maintain said tube in contact with said first electrode, and means for biasing said one surface of said one end of said electrolyte tube against said first electrode and comprising a hollow cap attached to said sleeve and a spring within said hollow cap bearing against the outer end of said electrolyte tube to press said one surface of said electrolyte tube against said first electrode to maintain good electrical contact therebetween, said first electrode comprising a chemically and thermodynamically stable electronic ceramic conductor means which is relatively inert to the electrolyte tube and said hot corrosive gas.

2. The measuring device of claim 1 in which said electronic ceramic conductor comprises cation-doped lanthanum chromite.

3. The measuring device of claim 2 in which said electronic ceramic conductor is compounded by the formula $La_{1-x}M_xCrO_3$ where M can be any cation having a valence of +2 and x is between 0 and 0.25.

4. The measuring device of claim 1, the improvement wherein said first electrode comprises a metallic conductor coated with a non-porous coating of an electronic ceramic conductor.

5. A gas measuring device for measuring a characteristic of hot corrosive gases comprising a support tube having an end wall, and having a solid electrolyte, means for mounting said electrolyte within said support tube spaced from said end wall with a portion of its surface exposed to the hot corrosive gas which is to be measured, and having first and second electrodes, and said second electrode being in contact with said exposed electrolyte surface and means pressing said electrode and electrolyte together, said first electrode being disc-shaped and formed from a chemically and thermodynamically stable electronic ceramic conductor which is relatively inert to the electrolyte tube and said hot corrosive gas, an electrical lead for said first electrode, said lead having a disc contacting portion, said disc being positioned in said support tube between said electrolyte and said end wall of said support tube and in electrical contact with said lead contacting portion, and refractory cement sealing said disc in said support tube and cooperating with said disc to isolate said lead contacting portion of said electrode from the hot furnace gases to prevent corrosion thereof.

6. The gas measuring device of claim 5 in which said electronic ceramic conductor is compounded by the formula $La_{1-x}M_xCrO_3$ where M is any cation having a valence of +2 and x is between 0 and 0.25.

7. The gas measuring device of claim 6 wherein the cation M is strontium.

8. The gas measuring device of claim 6 wherein the cation M is calcium.

9. The gas measuring device of claim 6 wherein the value of x is between 0.15 and 0.25.

10. The improvement of claim 5 wherein said disc has a surface in mechanical contact with said electrolyte exposed surface and with mechanical clearance therebetween to afford flow of gas between said disc surface and said electrolyte surface.

11. In a gas measuring device for measuring a characteristic of high temperature gases in a furnace and including a solid electrolyte and first and second electrodes, the improvement wherein said first electrode comprises a web portion and wing portions of a noble metal screen, a lead wire assembly including a main lead wire extending through and secured to said web portion, and second and third lead wires each having one end wrapped around said main lead wire and the other ends secured to said web portion at points spaced from said main lead, and said wing portions being folded over said web portion with said wing portions in overlapping relationship.

12. The improvement of claim 11 wherein said first electrode is coated with an electronic ceramic conductor.

13. In a gas measuring device for measuring a characteristic of high temperature gases in a furnace and including a solid electrolyte and first and second electrodes on opposite sides of said electrolyte, a support tube having a side wall, an end wall and partially enclosing said electrodes, and ports in said support tube to expose said electrolyte to the gases being measured, the improvement wherein said ports comprise opposed slots in said side wall which extend through the surface of said side wall and wherein said end wall has a recess and said first electrode being located in said recess, and cement securing said first electrode in said recess.

14. In a gas measuring device for measuring a characteristic of high temperature gases in a furnace and including a solid electrolyte and first and second electrodes, the improvement wherein said first electrode comprises a web portion and wing portions of a noble metal screen, a lead wire assembly secured to said web portion and said wing portions being folded over said web portion with said wing portions in overlapping relationship to enclose and protect the connection of said lead wire assembly to said web portion.

15. A gas measuring device for measuring a characteristic of high temperature gases comprising an electrolyte tube having an inside surface and an outside surface, said tube comprising a solid electrolyte material, mounting means for so mounting said tube that one of said surfaces is exposed to a hot corrosive gas whose characteristic is to be measured and the other said surface is exposed to a known reference gas, a first electrode, means for holding said first electrode in contact with said one surface, a second electrode, means for holding said second electrode in contact with said other surface, electrical conductors coupled to said electrodes, said mounting means including a projecting sleeve within which said electrolyte tube is slideable, and means for biasing said one surface against said first electrode to maintain good electrical contact therebetween, said first electrode having an electrical lead, and a non-porous coating of electronic ceramic conductor cement on said lead to protect said lead from hot furnace gases and form said electrode.

* * * * *